(12) United States Patent
Yamauchi et al.

(10) Patent No.: US 6,497,808 B1
(45) Date of Patent: Dec. 24, 2002

(54) GAS SENSOR

(75) Inventors: Masanobu Yamauchi, Kariya (JP); Kenji Fukaya, Chiryu (JP)

(73) Assignee: Denso Corporation, Aichi-Pref. (JP)

( * ) Notice: Subject to any disclaimer, the term of this patent is extended or adjusted under 35 U.S.C. 154(b) by 0 days.

(21) Appl. No.: 09/678,841

(22) Filed: Oct. 4, 2000

(30) Foreign Application Priority Data

Oct. 4, 1999 (JP) .......................................... 11-2831569

(51) Int. Cl.$^7$ ............................................ G01N 27/407
(52) U.S. Cl. ........................ 205/785; 204/408; 204/427; 204/428
(58) Field of Search ................................ 204/421–429, 204/408; 205/783.5–785

(56) References Cited

U.S. PATENT DOCUMENTS

| | | | |
|---|---|---|---|
| 4,049,524 A | * | 9/1977 | Togawa et al. |
| 4,096,048 A | * | 6/1978 | Matsumoto et al. |
| 4,155,828 A | * | 5/1979 | Takao et al. |
| 5,804,050 A | * | 9/1998 | Hayakawa et al. |

FOREIGN PATENT DOCUMENTS

| | | |
|---|---|---|
| JP | 4-157358 | 5/1992 |
| JP | 8-122297 | 5/1996 |

OTHER PUBLICATIONS

Hackh's Chemical Dictionary, 4$^{th}$ Ed., (1969), pp. 358–359.*
Handbook Of Chemistry and Physics, 55$^{th}$ Ed., (1974), pp. B89, B99.*

* cited by examiner

Primary Examiner—T. Tung
(74) Attorney, Agent, or Firm—Nixon & Vanderhye PC

(57) ABSTRACT

A gas sensor includes a sensor element. The sensor element has a solid electrolytic member, a measurement electrode, and a reference electrode. The measurement electrode is provided on the solid electrolytic member, and is exposed to a measurement gas. The reference electrode is provided on the solid electrolytic member, and is exposed to a reference gas. A heater operates for heating the sensor element. A portion of the heater contacts a portion of the sensor element. The temperature of the sensor element is increased to 300° C. by the heater in ten seconds after the start of activation of the heater.

5 Claims, 9 Drawing Sheets

GAS SENSOR

BACKGROUND OF THE INVENTION

1. Field of the Invention

This invention generally relates to a gas sensor. This invention relates to, for example, a gas sensor located in an exhaust system of an automotive internal combustion engine for measuring a specific-component concentration such as an oxygen concentration in an exhaust gas produced by the engine.

2. Description of the Related Art

The exhaust system of a typical internal combustion engine for an automotive vehicle is provided with a gas sensor to detect an oxygen concentration in an exhaust gas produced by the engine. The gas sensor includes a sensor element. In general, the sensor element has a solid electrolytic member, and a pair of a measurement electrode and a reference electrode extending on surfaces of the solid electrolytic member. The gas sensor outputs an electric signal representing the detected oxygen concentration in the exhaust gas. An engine control system adjusts conditions of the burning of an air-fuel mixture in the engine in response to the output signal of the gas sensor to implement fuel economy and exhaust emission control.

The sensor element within the gas sensor is active only when its temperature is equal to or higher than a given value. It is known to provide a heater in the gas sensor. The sensor element is heated to the given temperature or higher by the heater so that the gas sensor can operate from a moment immediately after the start of the engine.

In the case where high power is fed to the heater, the output signal from the gas sensor tends to contain considerable noise components immediately after the start of the engine. Such noise components cause wrong control of conditions of the burning of an air-fuel mixture in the engine.

Japanese published unexamined patent application 4-157358 discloses an oxygen sensor for detecting an oxygen concentration in an exhaust gas produced by an automotive internal combustion engine. The oxygen sensor includes a solid electrolytic member having a hollow cylindrical shape or a cup-like shape. A pair of electrodes are provided on inner and outer surfaces of the solid electrolytic member, respectively. A heater is disposed in the solid electrolytic member. An end of the heater contacts the inner surface of a bottom of the solid electrolytic member. The oxygen sensor is designed to fall into a correctly operating state in a short time after the start of the activation of the heater. In the oxygen sensor, a ratio Rh/Rs is equal to or greater than 0.8 where Rh denotes the outside diameter of the heater and Rs denotes the inside diameter of the solid electrolytic member. A ratio L/Rh is equal to or smaller than 2 where L denotes the axial length of a heating member in the heater. A ratio D/Rs is equal to or smaller than 0.6 where D denotes the distance between a lower end of the heating member and the inner surface of the bottom of the solid electrolytic member.

Japanese published unexamined patent application 8-122297 discloses an oxygen sensor including a solid electrolytic member having a cup-like shape or a hollow cylindrical shape. Inner and outer electrodes are provided on inner and outer surfaces of the solid electrolytic member, respectively. A heater is disposed in the solid electrolytic member. A high-emissivity layer is provided between the heater and the inner surface of the solid electrolytic member (or the inner electrode). The high-emissivity layer efficiently transmits heat from the heater to the solid electrolytic member.

SUMMARY OF THE INVENTION

It is an object of this invention to provide a gas sensor which can output a noise-free signal even at an initial operation stage.

A first aspect of this invention provides a gas sensor comprising a sensor element including a solid electrolytic member, a measurement electrode, and a reference electrode, the measurement electrode being provided on the solid electrolytic member and being exposed to a measurement gas, the reference electrode being provided on the solid electrolytic member and being exposed to a reference gas; a heater for heating the sensor element, wherein a portion of the heater contacts a portion of the sensor element; and means for enabling a temperature of the sensor element to be increased to 300° C. by the heater in ten seconds after a start of activation of the heater.

A second aspect of this invention is based on the first aspect thereof, and provides a gas sensor wherein a leak resistance RL between the heater and the sensor element, and an internal resistance Ri of the sensor element have a relation as follows:

$$\text{LOG}(RL/Ri) \geq 2$$

A third aspect of this invention is based on the first aspect thereof, and provides a gas sensor wherein the reference electrode faces the heater and contains a high-emissivity material.

A fourth aspect of this invention is based on the first aspect thereof, and provides a gas sensor wherein the heater has a blacked surface facing the sensor element.

DESCRIPTION OF THE PREFERRED EMBODIMENTS

First Embodiment

Figure 1:
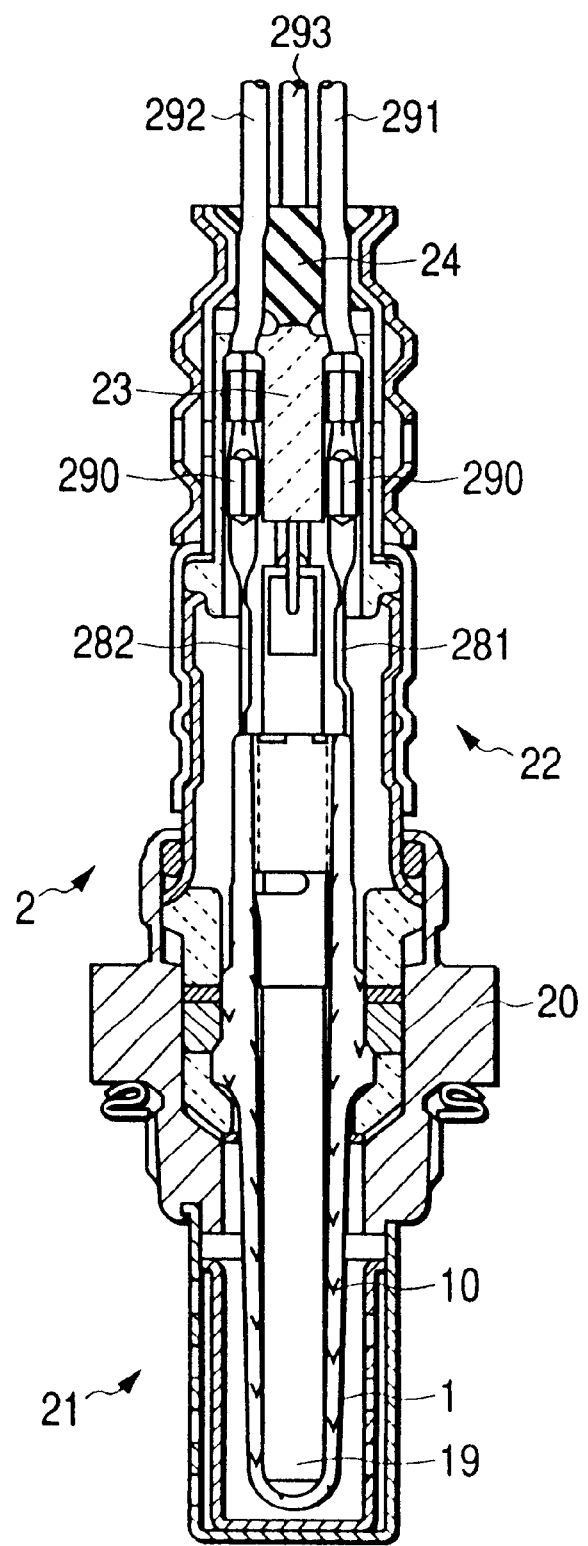
FIG. 1 is a longitudinal section view of a gas sensor according to a first embodiment of this invention.

FIG. 1 shows a gas sensor 2 according to a first embodiment of this invention. The gas sensor 2 is connected to the exhaust system of an automotive internal combustion engine. The gas sensor 2 detects, for example, an oxygen concentration in an exhaust gas produced by the engine.

As shown in FIG. 1, the gas sensor 2 includes a cylindrical housing 20 in which a sensor element 1 is fixedly disposed. A measurement-gas-side cover 21 having a double-wall structure is provided on the lower end (the front end) of the housing 20. The measurement-gas-side cover 21 has holes for introducing a measurement gas, that is, an engine exhaust gas. An atmosphere-side cover 22 having a triple-wall structure is provided on the upper end (the base end) of the housing 20. The atmosphere-side cover 22 has holes for introducing an atmosphere which is used as a reference gas. An insulator 23 and a resilient insulating member 24 are located in the atmosphere-side cover 22.

Signal transmission leads 291 and 292, and power feed leads 293 (only one of which is shown in FIG. 1) extend through the resilient insulating member 24. The leads 291 and 292 are connected to terminals 281 and 282 via metal connectors 290, respectively. Similarly, the lead 293 are connected to terminals via metal connectors. The metal connectors including the metal connectors 290 are located in holes of the insulator 23, respectively. The terminals including the terminals 281 and 282 are provided on the sensor element 1. The terminals 281 and 282 are connected to electrodes in the sensor element 1, respectively. The other electrodes, which connect with the leads 293, are connected to a heater 19 for the sensor element 1.

Figure 2:
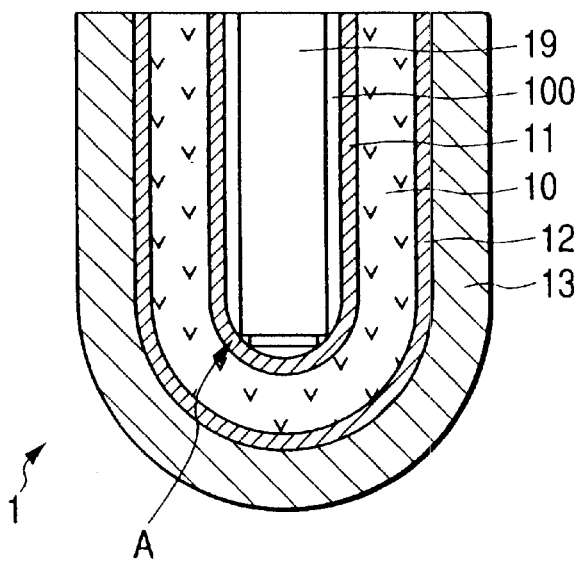
FIG. 2 is a longitudinal section view of a portion of a sensor element in FIG. 1.

As shown in FIGS. 1 and 2, the sensor element 1 includes a solid electrolytic member 10. The solid electrolytic member 10 can conduct oxygen ions. The solid electrolytic member 10 has a cup-like shape or a hollow cylindrical shape with a closed end, that is, a bottom. The solid electrolytic member 10 has an inner space 100 which is used as an atmosphere chamber. The atmosphere (the reference gas) is introduced into the inner space 100 in the solid electrolytic member 10.

The sensor element 1 also includes a pair of a reference electrode 11 and a measurement electrode 12. The reference electrode 11 is provided on the inner surfaces of the solid electrolytic member 10 which are exposed in the atmosphere chamber 100. The measurement electrode 12 is provided on the outer surfaces of the solid electrolytic member 10 which are exposed to the measurement gas (the exhaust gas). The measurement electrode 12 is covered with a protective layer 13 which can conduct the measurement gas. The reference electrode 11 and the measurement electrode 12 are connected to the terminals 281 and 282, respectively.

The gas sensor 2 includes a rod-like heater 19 disposed in the atmosphere chamber 100 of the sensor element 1. The heater 19 generates heat when being fed with electric power. The device 19 operates to heat the sensor element 1. Portions of the heater 19 and the sensor element 1 contact each other so that the heater 19 can efficiently heat the sensor element 1. Specifically, the heater 10 increases the temperature of the sensor element 1 to 300° C. in a time of 10 seconds after the start of the power feed thereto. Opposite ends of the heater 19 are connected to the terminals which are associated with the leads 293. Accordingly, electric power can be fed from an external power supply to the heater 19 via the leads 293.

The heater 19 is made of ceramic. A heating member is contained in a lower portion (a front portion) of the heater 19. As shown in FIG. 2, the outer portion "A" of the lower end (the front end) of the heater 19 contacts the inner surfaces of the reference electrode 11 or the solid electrolytic member 10 which define the atmosphere chamber 100.

Figure 3:
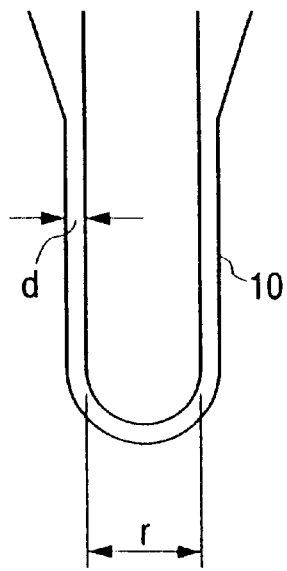
FIG. 3 is a longitudinal section view of a portion of a solid electrolytic member in the gas sensor of FIG. 1.

With reference to FIG. 3, a lower portion (a front portion) of the solid electrolytic member 10 except the bottom extends straight along the axial direction, and has a uniform cross-section. The walls of the lower portion of the solid electrolytic member 10 have a thickness "d" of 0.5 mm. The inside diameter "r" of the lower portion of the solid electrolytic member 10 is equal to 3.6 mm.

Figure 4:
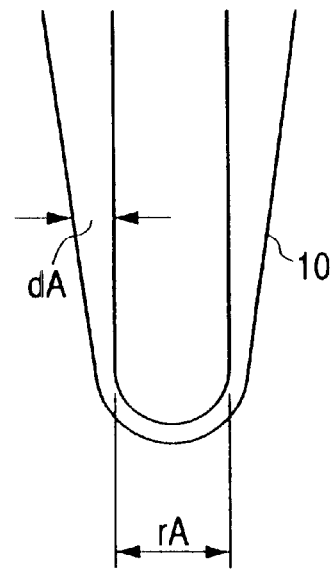
FIG. 4 is a longitudinal section view of a portion of a solid electrolytic member in a comparative gas sensor.

A comparative gas sensor was made. The comparative gas sensor was similar to the gas sensor 2 except that a solid electrolytic member 10A replaced the solid electrolytic member 10. The solid electrolytic member 10A had a tapered shape as shown in FIG. 4. The mean thickness "dA" of the walls of a lower portion (a front portion) of the solid electrolytic member 10A was equal to 0.9 mm. The inside diameter "rA" of the lower portion of the solid electrolytic member 10A was equal to 3.6 mm.

Experiments were performed. Thermocouples were connected to the heater 19 and the sensor element 1. During the experiments, the temperatures of the heater 19 and the sensor element 1 were measured via the thermocouples while the heater 19 was activated by dc power having a voltage of 14 V. Similarly, the temperatures of a heater and a sensor element in the comparative gas sensor were measured.

Figure 5:
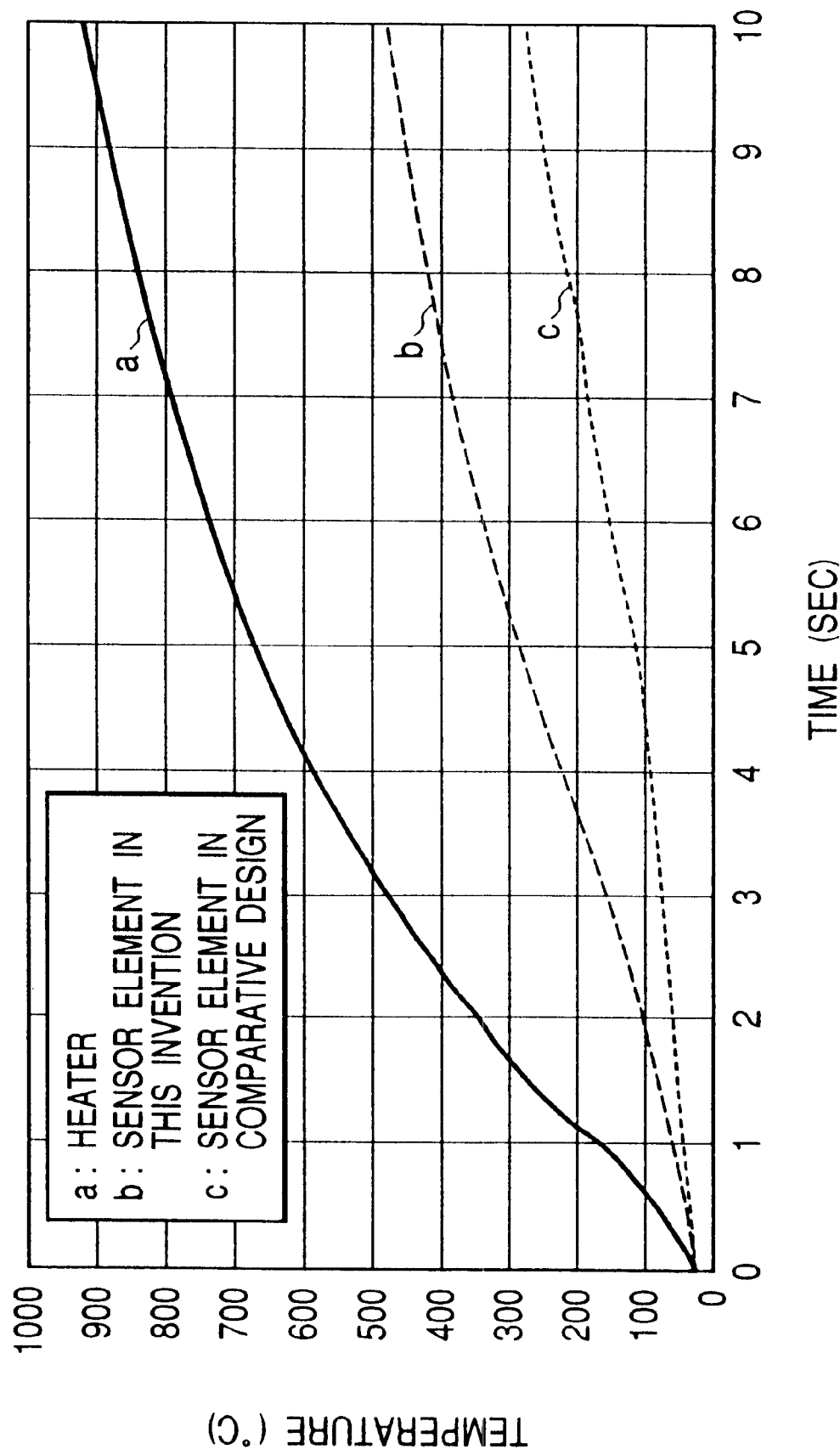
FIG. 5 is a diagram of the temperature of a heater, the temperature of the sensor element in FIGS. 1 and 2, and the temperature of a sensor element in the comparative gas sensor which vary in accordance with the duration of the activation of the heater.

With reference to FIG. 5, the measured temperature of the heater 19 rose along the curve "a" in accordance with the duration of the activation of the heater 19, that is, the lapse of time from the start of the activation of the heater 19. The measured temperature of the sensor element 1 rose along the curve "b" in accordance with the duration of the activation of the heater 19 (the lapse of time from the start of the activation of the heater 19). The measured temperature of the heater in the comparative gas sensor rose along the curve "a" in accordance with the duration of the activation of the heater (the lapse of time from the start of the activation of the heater). The measured temperature of the sensor element in the comparative gas sensor rose along the curve "c" in accordance with the duration of the activation of the heater (the lapse of time from the start of the activation of the heater).

As shown in FIG. 5, the measured temperature of the sensor element 1 reached 300° C. about five seconds after the start of the activation of the heater 19. On the other hand, the measured temperature of the sensor element in the comparative gas sensor did not reach 300° C. even ten seconds after the start of the activation of the heater.

The voltage of the output signal from the gas sensor 2 was measured under conditions where the sensor element 1 was exposed to a reference ambient gas ($\lambda>1$) and the heater 19 was activated by dc power having a voltage of 14 V. Similarly, the voltage of the output signal from the comparative gas sensor was measured.

Figure 6:
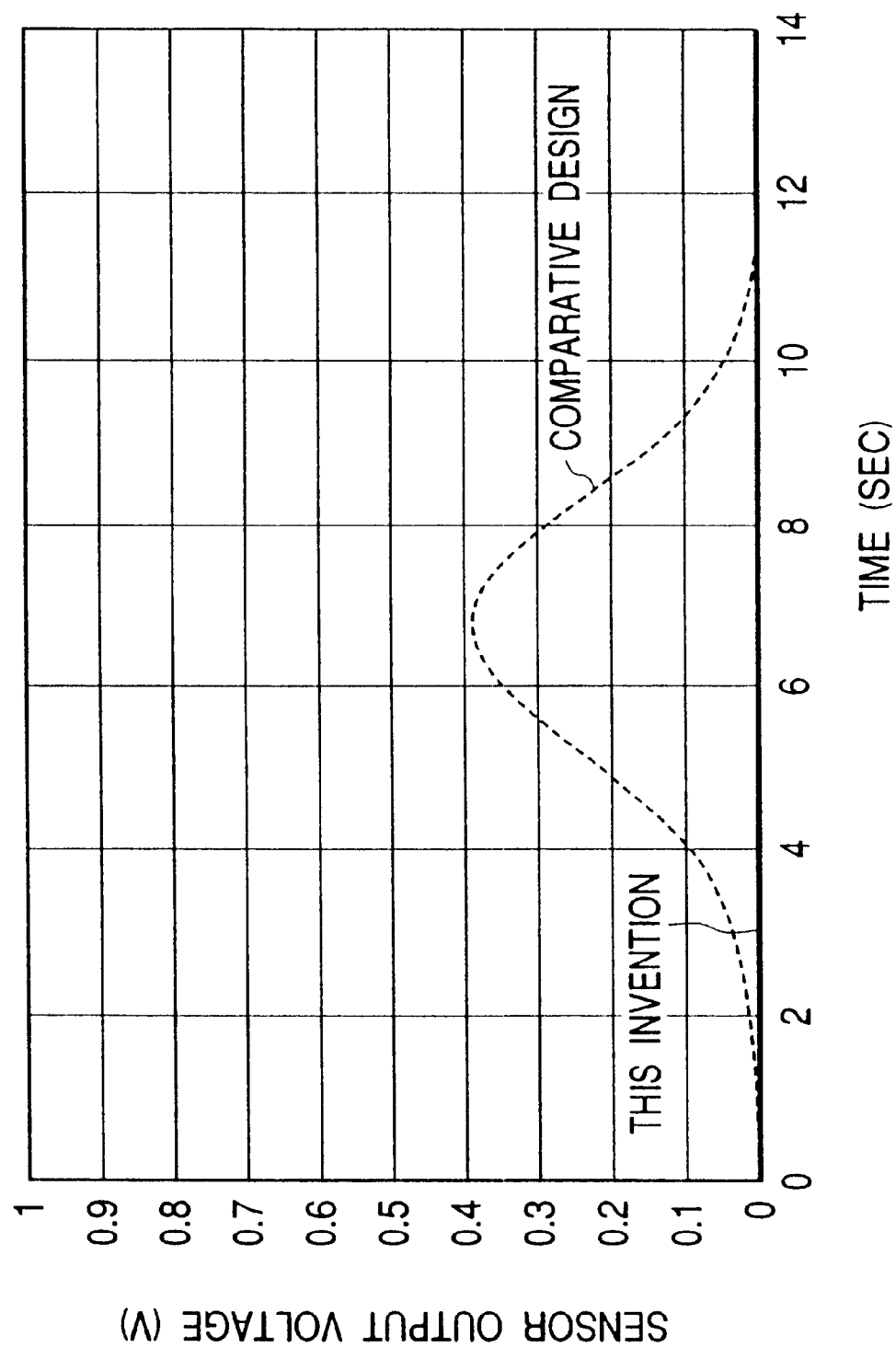
FIG. 6 is a diagram of the voltage of the output signal from the gas sensor in FIG. 1 and the voltage of the output signal from the comparative gas sensor which occur while the duration of the activation of the heater increases from zero to fourteen seconds.

With reference to FIG. 6, the measured voltage of the output signal from the gas sensor 2 remained small and did not exhibit any abnormality as the duration of the activation of the heater 19 (that is, the lapse of time from the start of the activation of the heater 19) increased to fourteen seconds. On the other hand, the measured voltage of the output signal from the comparative gas sensor exhibited a considerable peak, that is, an abnormality while the duration of the activation of the heater (the lapse of time from the start of the activation of the heater) increased from two seconds to eleven seconds.

Figure 7:
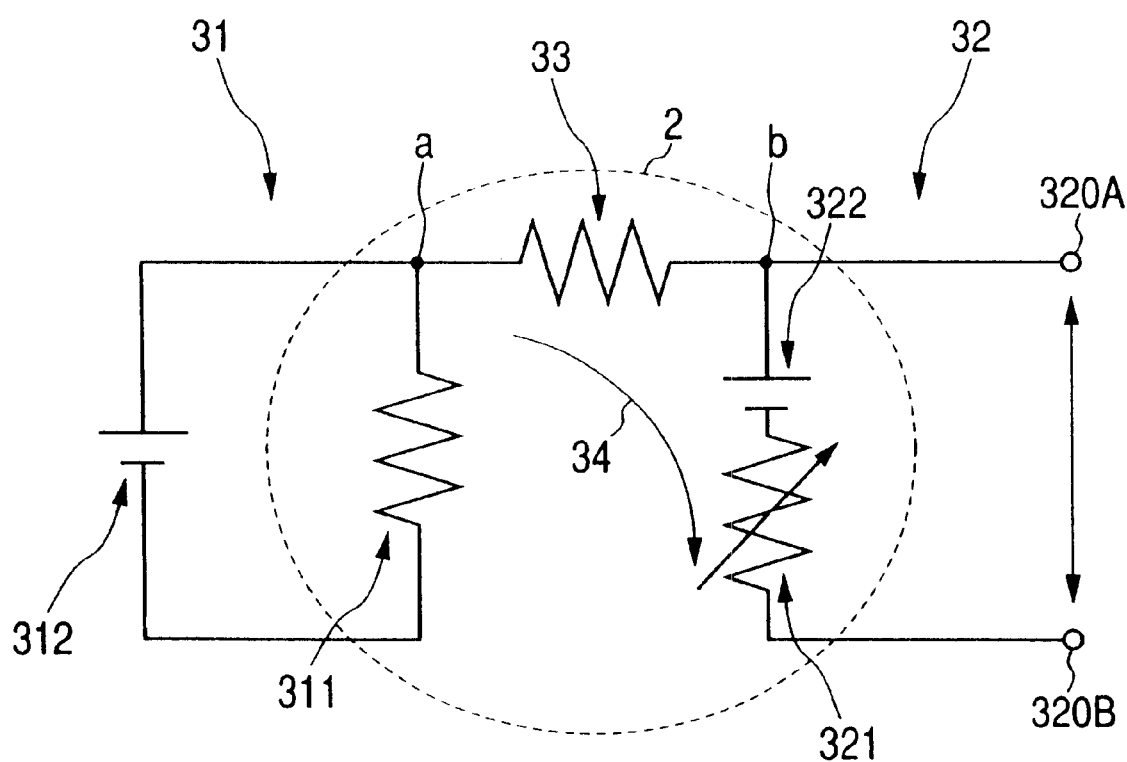
FIG. 7 is a schematic diagram of an equivalent circuit of the gas sensor in FIG. 1 and a heater power supply.

FIG. 7 shows an equivalent circuit of the gas sensor 2. The equivalent circuit of the gas sensor 2 includes a heater equivalent circuit 31 and a sensor-element equivalent circuit 32. The heater equivalent circuit 31 is composed of a dc heater power supply 312 and a resistor 311 corresponding to the resistance 311 of the heater 19. The positive terminal of the power supply 312 is connected to one end of the heater resistor 311. The negative terminal of the power supply 312 is connected to the other end of the heater resistor 311. The sensor-element equivalent circuit 32 is composed of output terminals 320A and 320B, a resistor 321 corresponding to the internal resistance of the sensor element 1, and a sensor-element power supply (an electromotive force) 322. The positive terminal of the power supply 322 is connected to the output terminal 320A. The negative terminal of the power supply 322 is connected to one end of the internal resistor 321. The other end of the internal resistor 321 is connected to the output terminal 320B. The output signal of the sensor element 1 (that is, the output signal of the gas sensor 2) appears between the output terminals 320A and 320B.

As previously mentioned, the outer portion "A" of the lower end of the heater 19 contacts the inner surfaces of the reference electrode 11 or the solid electrolytic member 10 which define the atmosphere chamber 100 (see FIG. 2). Thus, a portion of the heater 19 contacts a portion of the sensor element 1. Accordingly, as shown in FIG. 7, the heater equivalent circuit 31 and the sensor-element equivalent circuit 32 are connected to each other through a leak resistor 33. Specifically, one end of the leak resistor 33 is connected to the junction between the positive terminal of the heater power supply 312 and the related end of the heater resistor 311. The other end of the leak resistor 33 is connected to the junction between the positive terminal of the sensor-element power supply 322 and the output terminal 320A. Accordingly, a current 34 can leak from the heater equivalent circuit 31 to the sensor-element equivalent circuit 32 through the leak resistor 33. The leak current 34 is caused by the heater power supply 312.

In FIG. 7, the heater resistor 311, the leak resistor 33, the internal resistor 321, and the sensor-element power supply 322 are contained in the gas sensor 2.

When the heater 19 is supplied with electric power from the heater power supply 312, the leak current 34 flows from the heater equivalent circuit 31 to the sensor element equivalent circuit 32 through the leak resistor 33. The abnormal output voltage Vo from the sensor element 1 is expressed as follows.

$$Vo=\{Ri/(Ri+RL)\}\cdot VL=\{1/(1+RL/Ri)\}\cdot VL \quad (1)$$

where RL denotes the resistance of the leak resistor 33 and VL denotes the leak voltage related to the leak current 34, and Ri denotes the internal resistance of the sensor element 1. The equation (1) reveals that the abnormal output voltage Vo from the sensor element 1 decreases as the ratio "RL/Ri" increases.

Figure 8:
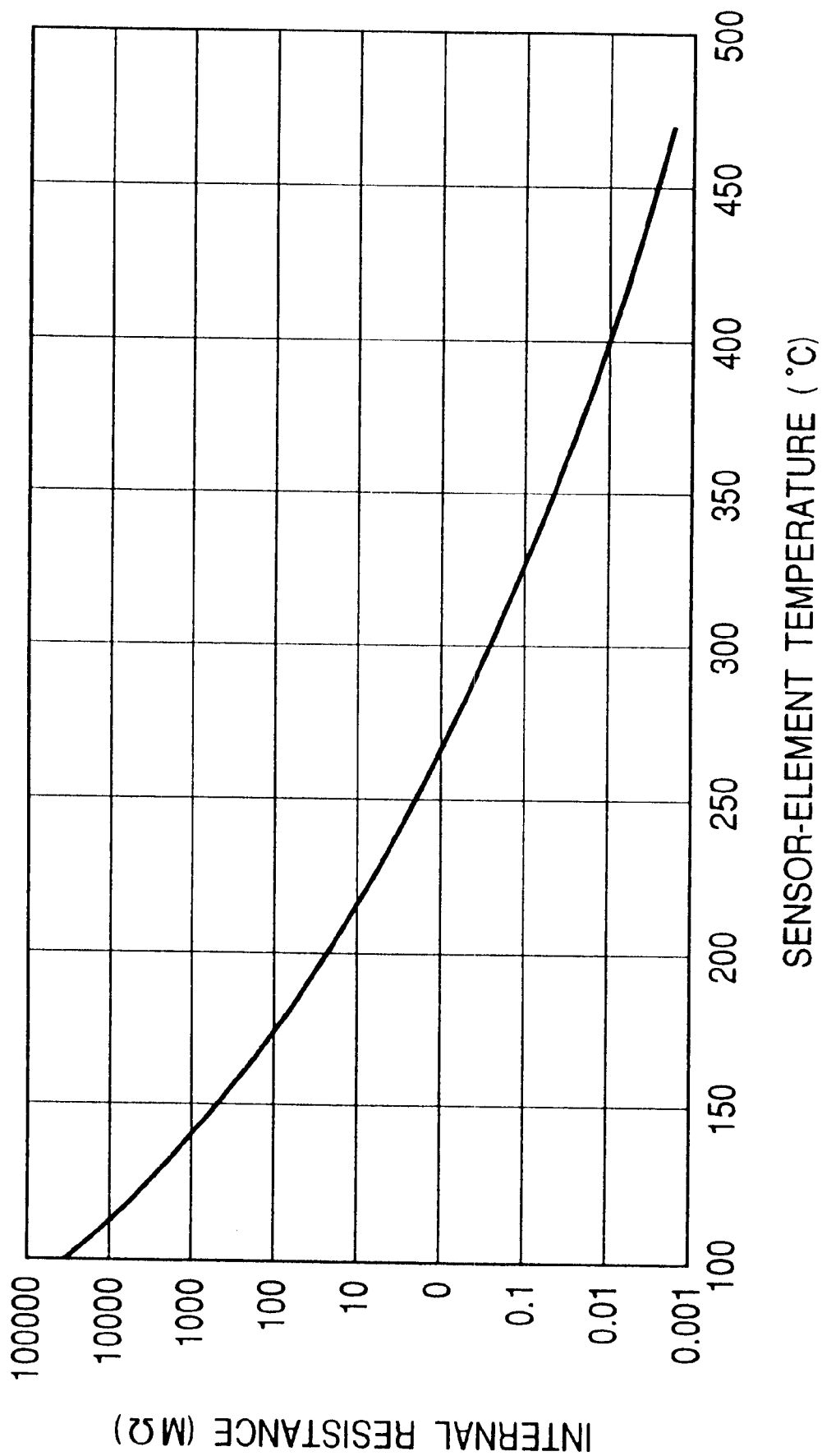
FIG. 8 is a diagram of the relation between the internal resistance of the sensor element and the temperature thereof in the gas sensor of FIG. 1.

Experiments were performed. During the experiments, the temperature of the sensor element 1 and the internal resistance thereof were measured while the heater 19 was activated. With reference to FIG. 8, the measured internal resistance of the sensor element 1 dropped as the temperature thereof increased. The measured internal resistance of the sensor element 1 was in the range of 0.1 MΩ to 1 MΩ when the temperature thereof was equal to 300° C.

Figure 9:
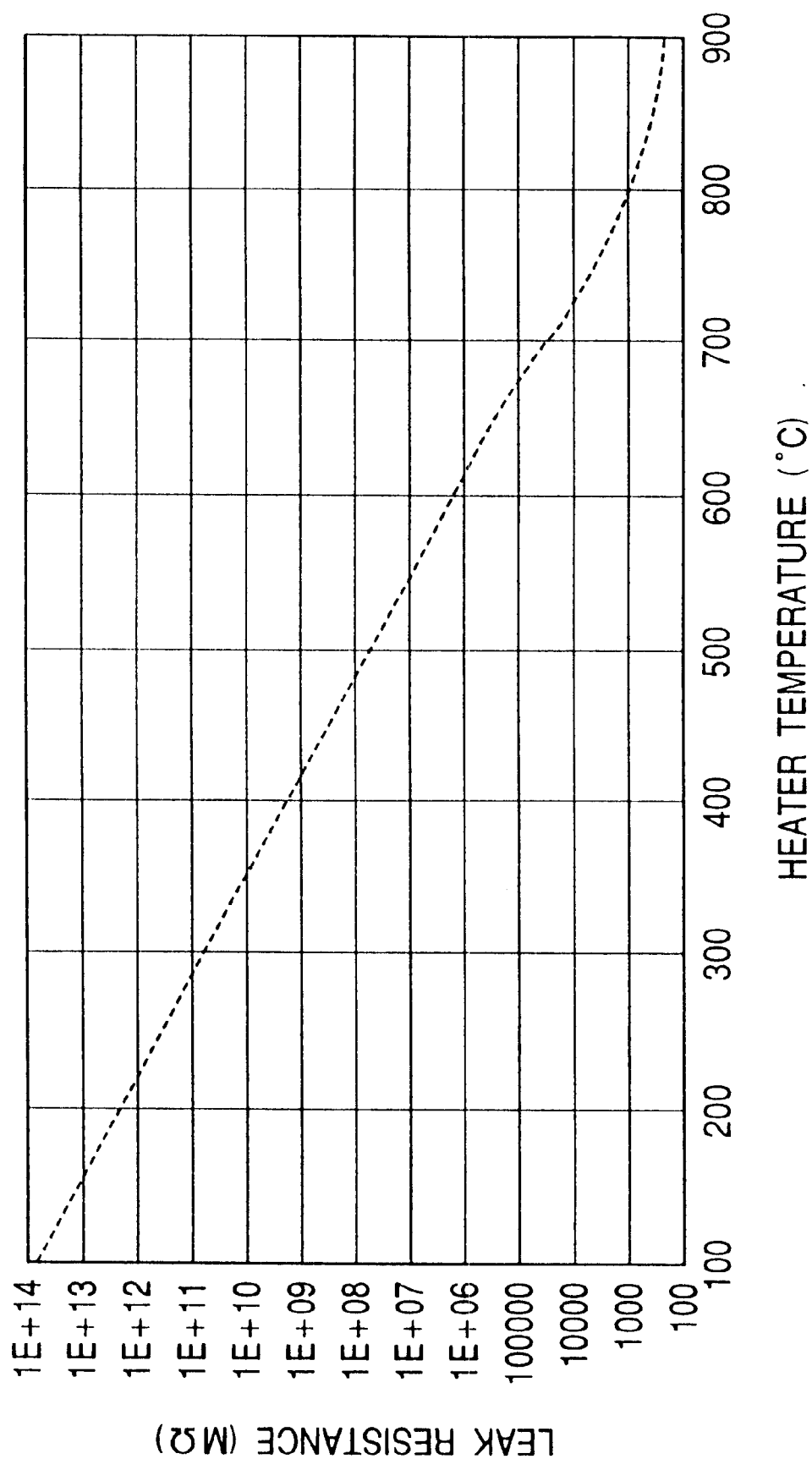
FIG. 9 is a diagram of the relation between a leak resistance and the temperature of the heater in the gas sensor of FIG. 1.

The leak resistance, that is, the resistance of the leak resistor 33, is estimated in consideration of experiment results. With reference to FIG. 9, the leak resistance drops as the temperature of the heater 19 rises.

Experiments were performed. During the experiments, the resistance of the heater 19 and the internal resistance of the sensor element 1 were measured while the heater 19 was activated by dc power having a voltage of 14 V. Similarly, the resistance of the heater and the internal resistance of the sensor element in the comparative gas sensor were measured.

Figure 10:
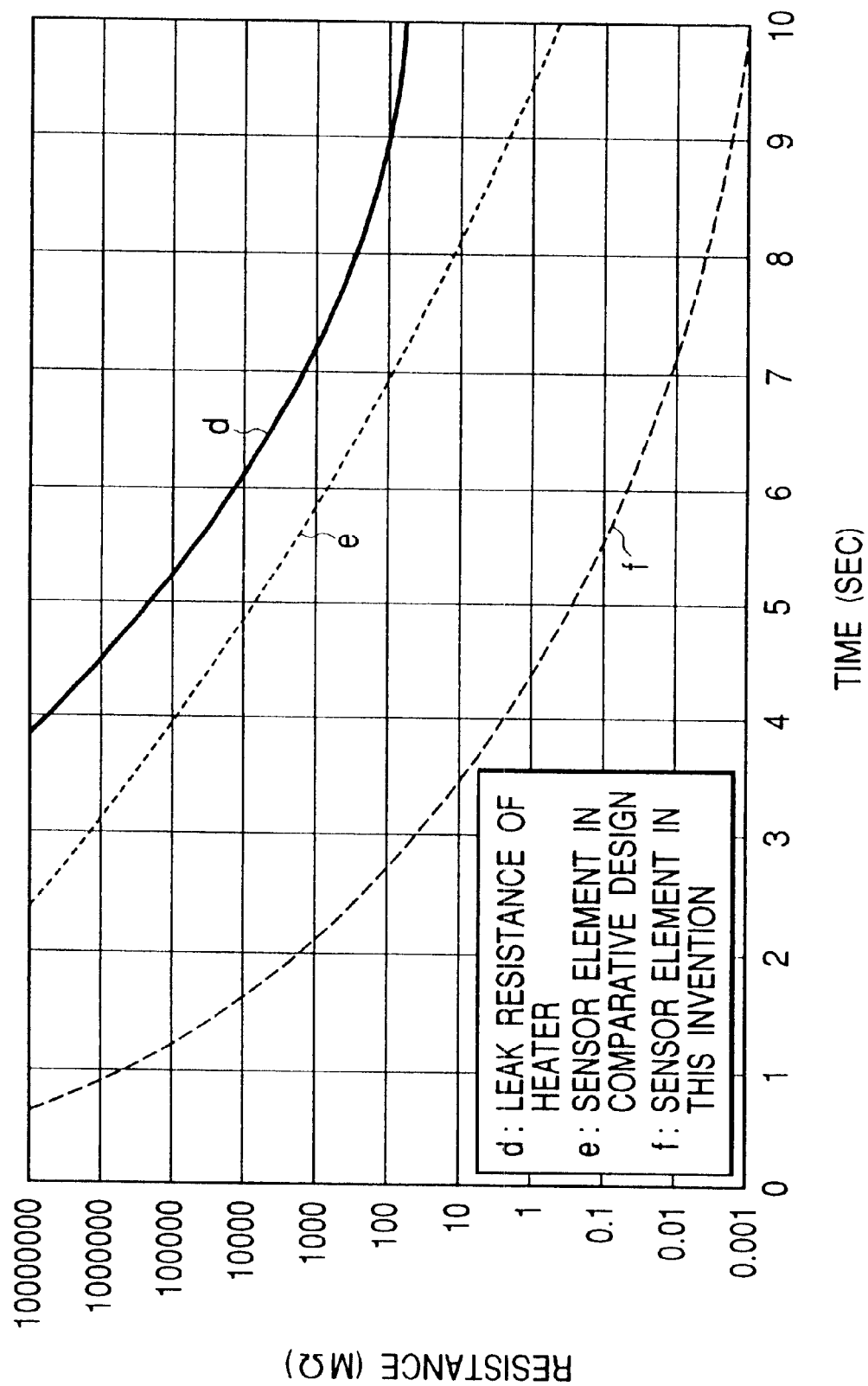
FIG. 10 is a diagram of the leak resistance of the heater, the internal resistance of the sensor element in the gas sensor of FIG. 1, and the internal resistance of the sensor element in the comparative gas sensor which occur while the duration of the activation of the heater increases from zero to ten seconds.

With reference to FIG. 10, the measured resistance of the heater 19 dropped along the curve "d" in accordance with the duration of the activation of the heater 19, that is, the lapse of time from the start of the activation of the heater 19. Similarly, the measured resistance of the heater in the comparative gas sensor dropped in accordance with the duration of the activation of the heater (the lapse of time from the start of the activation of the heater). The measured internal resistance of the sensor element 1 dropped along the curve "f" in accordance with the duration of the activation of the heater 19 (the lapse of time from the start of the activation of the heater 19). About five seconds after the start of the activation of the heater 19, the measured internal resistance of the sensor element 1 reached a value corresponding to a temperature of 300° C. The measured internal resistance of the sensor element in the comparative gas sensor dropped along the curve "e" in accordance with the duration of the activation of the heater (the lapse of time from the start of the activation of the heater). Even ten seconds after the start of the activation of the heater, the measured internal resistance of the sensor element in the comparative gas sensor did not reach a value corresponding to a temperature of 300° C.

The gas sensor 2 is designed so that the temperature of the sensor element 1 rises to 300° C. within about ten seconds after the start of the activation of the heater 19 but without electrical noise being generated. This feature is made possible by certain design features such as explained below.

The surfaces of the sensor element 1 (the surfaces of the reference electrode 11 or the surfaces of the solid electrolytic member 10) which face the heater 19 are provided with a high-emissivity layer. The high-emissivity layer means a layer having a high thermal emissivity or a layer having a high ability to transmit heat. It should be noted that the high-emissivity layer may be provided between the heater 19 and the sensor element 1. The high-emissivity layer conducts gases. The high-emissivity layer is made of porous material having a high thermal emissivity. The reference gas can reach the reference electrode 11 from the atmosphere chamber 100 through the high-emissivity layer.

Preferably, the material for the high-emissivity layer is at least one selected from among alumina, titanium oxide, zirconia, iron oxide, nickel oxide, manganese oxide, copper oxide, cobalt oxide, chromium oxide, yttrium oxide, cordierite, silicon oxide, aluminum nitride, and silicon carbide.

The reference electrode 11 may be made from a mixture of a basic electrode material and a high-emissivity material. In this case, the completed reference electrode 11 has a high emissivity. Preferably, the high-emissivity material is at least one selected from among alumina, titanium oxide, zirconia, iron oxide, nickel oxide, manganese oxide, copper oxide, cobalt oxide, chromium oxide, yttrium oxide, cordierite, silicon oxide, aluminum nitride, and silicon carbide.

The volume of the sensor element 1 is set to or smaller than a given value. The thermal capacity of the sensor element 1 is set to or smaller a given value. Specifically, the walls of the lower portion of the solid electrolytic member 10 have a relatively small thickness, for example, about 0.5 mm or less, to provide a small thermal capacity of the sensor element 1.

The outer surfaces of the heater 19 which face the reference electrode 11 or the solid electrolytic member 10 are blacked to efficiently transmit heat from the heater 19 to the sensor element 1. In addition, the heater 19 and the sensor element 1 are close to each other to efficiently transmit heat from the heater 19 to the sensor element 1.

To prevent the gas sensor 2 from outputting an abnormal signal, it is preferable that the leak resistance RL and the internal resistance Ri of the sensor element 1 have the following relation.

$$\mathrm{Log}(RL/Ri) \geq 2$$

Second Embodiment

A gas sensor of a second embodiment of this invention is similar to the gas sensor 2 (see FIG. 1) of the first embodiment thereof except for design changes indicated hereinafter. The gas sensor of the second embodiment of this invention includes a sensor element 1A instead of the sensor element 1 (see FIGS. 1 and 2).

Figure 11:
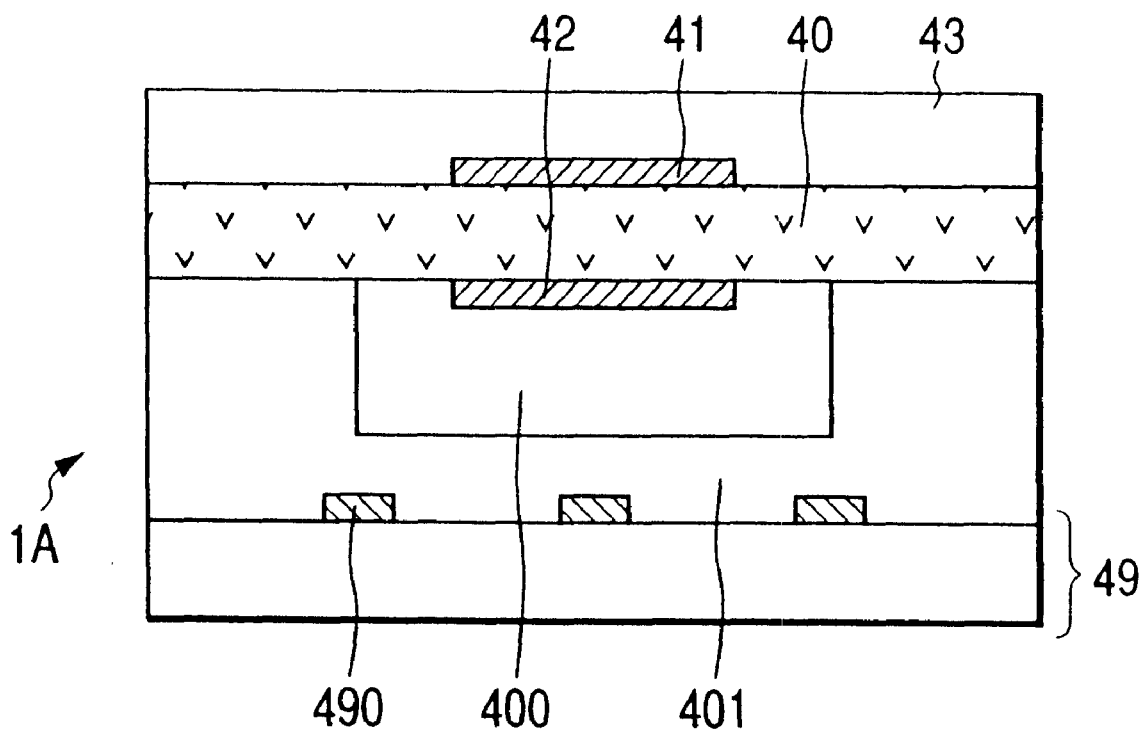
FIG. 11 is a sectional view of a sensor element in a gas sensor according to a second embodiment of this invention.

As shown in FIG. 11, the sensor element 1A is of a laminate type or a multiple-layer type. The sensor element 1A includes a solid electrolytic member 40 having a shape of a flat plate. A measurement electrode 41 is provided on the upper surface of the solid electrolytic member 40. A reference electrode 42 is provided on the lower surface of the solid electrolytic member 40. The measurement electrode 41 and the reference electrode 42 form a pair. The measurement electrode 41 and a portion of the upper surface of the solid electrolytic member 40 are covered with a protective porous layer 43. The reference electrode 42 is exposed in an atmosphere chamber 400. A spacer 401 provided on the lower surface of the solid electrolytic member 40 has a groove for forming the atmosphere chamber 400. A heater 49 is provided on the lower surface of the spacer 401. The heater 49 contains a heating member 490 adjoining the spacer 401.

OTHER EMBODIMENTS

The gas sensor of the first or second embodiment of this invention may be modified to an air-to-fuel ratio sensor, a NOx sensor, a CO sensor, or an HC sensor.

What is claimed is:

1. A gas sensor comprising:

a sensor element including a solid electrolytic member, a measurement electrode, and a reference electrode, the measurement electrode being provided on the solid electrolytic member and being exposed to a measurement gas, the reference electrode being provided on the solid electrolytic member and being exposed to a reference gas;

a ceramic heater for heating the sensor element, wherein a portion of the heater contacts a portion of the reference electrode of the sensor element; and means for enabling a temperature of the sensor element to be increased to 300° C. by the heater in ten seconds after a start of activation of the heater;

wherein a leak resistance RL between the heater and the sensor element, and an internal resistance Ri of the sensor element have a relation as follows:

$$\mathrm{Log}(RL/Ri) \geq 2.$$

2. A gas sensor as in claim 1, wherein the reference electrode faces the heater and contains a material selected from the group consisting of alumina, titanium oxide, zirconia, iron oxide, nickel oxide, manganese oxide, copper oxide, cobalt oxide, chromium oxide, yttrium oxide, cordierite, silicon oxide, aluminum nitride, and silicon carbide.

3. A gas sensor as in claim 1, wherein the heater has a blacked surface facing the sensor element.

4. A gas sensor comprising:

a solid electrolytic member having measurement and reference electrodes; said electrolytic member having an internal electrical resistance $R_i$;

an electrically powered ceramic heater disposed in contact with at least one of said electrodes and having an electrical leakage resistance RL thereto; and means for maintaining $\mathrm{Log}(RL/Ri) \geq 2$ during initial activation of the sensor as it is being brought to a normal operating temperature.

5. A method for using a gas sensor comprising a solid electrolytic member having measurement and reference electrodes; said electrolytic member having an internal electrical resistance $R_i$; and an electrically powered ceramic heater disposed in contact with at least one of said electrodes and having an electrical leakage resistance RL thereto, said method comprising:

maintaining $\mathrm{Log}(RL/Ri) \geq 2$ during initial activation of the sensor as it is being brought to a normal operating temperature.

* * * * *

UNITED STATES PATENT AND TRADEMARK OFFICE
CERTIFICATE OF CORRECTION

PATENT NO.    : 6,497,808 B1  Page 1 of 1
DATED         : December 24, 2002
INVENTOR(S)   : Yamauchi et al.

It is certified that error appears in the above-identified patent and that said Letters Patent is hereby corrected as shown below:

<u>Title page,</u>
Item [30], should read:
-- (30)  Foreign Application Priority Data

Oct. 4, 1999 (JP)............................11-283156 --

Signed and Sealed this

Twenty-ninth Day of April, 2003

JAMES E. ROGAN
*Director of the United States Patent and Trademark Office*